US008877914B2

(12) United States Patent
Berzofsky et al.

(10) Patent No.: US 8,877,914 B2
(45) Date of Patent: Nov. 4, 2014

(54) COMPOSITIONS COMPRISING NUCLEIC ACIDS ENCODING HIV-1 REVERSE TRANSCRIPTASE CTL EPITOPES

(75) Inventors: Jay A. Berzofsky, Bethesda, MD (US); Takahiro Okazaki, Yokohama (JP)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 298 days.

(21) Appl. No.: 12/796,614

(22) Filed: Jun. 8, 2010

(65) Prior Publication Data

US 2010/0322954 A1 Dec. 23, 2010

Related U.S. Application Data

(63) Continuation of application No. 10/551,405, filed as application No. PCT/US2004/009617 on Mar. 29, 2004, now Pat. No. 7,731,971.

(60) Provisional application No. 60/459,507, filed on Mar. 31, 2003.

(51) Int. Cl.

| | |
|---|---|
| ***C07H 21/04*** | (2006.01) |
| ***A61K 39/21*** | (2006.01) |
| ***A61K 39/385*** | (2006.01) |
| ***C07K 14/005*** | (2006.01) |
| *A61K 39/00* | (2006.01) |

(52) U.S. Cl.

CPC ........... *C07K 14/005* (2013.01); *A61K 2039/57* (2013.01); *A61K 2039/53* (2013.01); *A61K 39/385* (2013.01); *A61K 2039/645* (2013.01); *C12N 2740/16234* (2013.01); *A61K 2039/6018* (2013.01); *C12N 2740/16222* (2013.01); *A61K 39/21* (2013.01); *A61K 2039/5158* (2013.01)

USPC .................................... 536/23.72; 424/188.1

(58) Field of Classification Search

None

See application file for complete search history.

(56) References Cited

PUBLICATIONS

Betts, M. R., and A. Harari, 2008, Phenotype and function of protective T-cell immune responses in HIV, Curr. Opin. HIV AIDS 3:349-355.*

Connick, E., et al., 2007, CTL fail to accumulate at sites of HIV-1 replication in lymphoid tissue, J. Immunol. 178:6975-6983.*

Gallo, R. C., 2005, The end or the beginning of the drive to an HIV-preventive vaccine: a view from over 20 years, The Lancet 366:1894-1898.*

Walker, B. D., and D. R. Burton, 2008, Toward an AIDS vaccine, Science 320:760-764.*

* cited by examiner

*Primary Examiner* — Jeffrey Parkin

(74) *Attorney, Agent, or Firm* — Kilpatrick Townsend & Stockton LLP

(57) ABSTRACT

The present invention provides compositions comprising a vector including a nucleic acid comprising a nucleotide sequence encoding a peptide having the sequence $X_1$LYQYMDDV, wherein $X_1$ is any hydrophobic amino acid. The compositions are used to induce an immune response against human immunodeficiency virus (HIV).

2 Claims, 6 Drawing Sheets

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      immunostimulating peptide
<220> FEATURE:
<221> NAME/KEY: MOD_RES
<222> LOCATION: (1)
<223> OTHER INFORMATION: Xaa = any hydrophobic amino acid

<400> SEQUENCE: 1

Xaa Leu Tyr Gln Tyr Met Asp Asp Val
  1               5


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      immunostimulating peptide, RT-2L9V, 2L9V

<400> SEQUENCE: 2

Val Leu Tyr Gln Tyr Met Asp Asp Val
  1               5


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      immunostimulating peptide, RT-1Y2L9V
```

-continued

<400> SEQUENCE: 3

Tyr Leu Tyr Gln Tyr Met Asp Asp Val
1 5

<210> SEQ ID NO 4
<211> LENGTH: 409
<212> TYPE: PRT
<213> ORGANISM: Artificial Sequence
<220> FEATURE:
<223> OTHER INFORMATION: Description of Artificial Sequence:variant of synthetic sequence motif derived from HIV-1 reverse transcriptase (RT) catalytic site region, immunostimulating peptide
<220> FEATURE:
<221> NAME/KEY: MOD_RES
<222> LOCATION: (1)..(200)
<223> OTHER INFORMATION: Xaa = any amino acid, may be present or absent
<220> FEATURE:
<221> NAME/KEY: MOD_RES
<222> LOCATION: (201)
<223> OTHER INFORMATION: Xaa = any hydrophobic amino acid
<220> FEATURE:
<221> NAME/KEY: MOD_RES
<222> LOCATION: (210)..(409)
<223> OTHER INFORMATION: Xaa = any amino acid, may be present or absent

<400> SEQUENCE: 4

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Xaa Xaa Leu Tyr Gln Tyr Met Asp Asp
195 200 205

Val Xaa Xaa Xaa Xaa Xaa Xaa Xaa Xaa Xaa Xaa Xaa Xaa Xaa Xaa Xaa
210 215 220

Xaa Xaa Xaa Xaa Xaa Xaa Xaa Xaa Xaa Xaa Xaa Xaa Xaa Xaa Xaa Xaa
225 230 235 240

Xaa Xaa Xaa Xaa Xaa Xaa Xaa Xaa Xaa Xaa Xaa Xaa Xaa Xaa Xaa Xaa
245 250 255

Xaa Xaa Xaa Xaa Xaa Xaa Xaa Xaa Xaa Xaa Xaa Xaa Xaa Xaa Xaa Xaa

```
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa
                405


<210> SEQ ID NO 5
<211> LENGTH: 409
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      immunostimulating peptide
<220> FEATURE:
<221> NAME/KEY: MOD_RES
<222> LOCATION: (1)..(200)
<223> OTHER INFORMATION: Xaa = any amino acid, may be present or absent
<220> FEATURE:
<221> NAME/KEY: MOD_RES
<222> LOCATION: (210)..(409)
<223> OTHER INFORMATION: Xaa = any amino acid, may be present or absent

<400> SEQUENCE: 5

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160
```

-continued

```
Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Val Leu Tyr Gln Tyr Met Asp Asp
        195                 200                 205

Val Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa
                405
```

<210> SEQ ID NO 6
<211> LENGTH: 409
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      immunostimulating peptide
<220> FEATURE:
<221> NAME/KEY: MOD_RES
<222> LOCATION: (1)..(200)
<223> OTHER INFORMATION: Xaa = any amino acid, may be present or absent
<220> FEATURE:
<221> NAME/KEY: MOD_RES
<222> LOCATION: (210)..(409)
<223> OTHER INFORMATION: Xaa = any amino acid, may be present or absent

<400> SEQUENCE: 6

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45
```

-continued

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Xaa Tyr Leu Tyr Gln Tyr Met Asp Asp
195 200 205

Val Xaa Xaa Xaa Xaa Xaa Xaa Xaa Xaa Xaa Xaa Xaa Xaa Xaa Xaa Xaa
210 215 220

Xaa Xaa Xaa Xaa Xaa Xaa Xaa Xaa Xaa Xaa Xaa Xaa Xaa Xaa Xaa Xaa
225 230 235 240

Xaa Xaa Xaa Xaa Xaa Xaa Xaa Xaa Xaa Xaa Xaa Xaa Xaa Xaa Xaa Xaa
245 250 255

Xaa Xaa Xaa Xaa Xaa Xaa Xaa Xaa Xaa Xaa Xaa Xaa Xaa Xaa Xaa Xaa
260 265 270

Xaa Xaa Xaa Xaa Xaa Xaa Xaa Xaa Xaa Xaa Xaa Xaa Xaa Xaa Xaa Xaa
275 280 285

Xaa Xaa Xaa Xaa Xaa Xaa Xaa Xaa Xaa Xaa Xaa Xaa Xaa Xaa Xaa Xaa
290 295 300

Xaa Xaa Xaa Xaa Xaa Xaa Xaa Xaa Xaa Xaa Xaa Xaa Xaa Xaa Xaa Xaa
305 310 315 320

Xaa Xaa Xaa Xaa Xaa Xaa Xaa Xaa Xaa Xaa Xaa Xaa Xaa Xaa Xaa Xaa
325 330 335

Xaa Xaa Xaa Xaa Xaa Xaa Xaa Xaa Xaa Xaa Xaa Xaa Xaa Xaa Xaa Xaa
340 345 350

Xaa Xaa Xaa Xaa Xaa Xaa Xaa Xaa Xaa Xaa Xaa Xaa Xaa Xaa Xaa Xaa
355 360 365

Xaa Xaa Xaa Xaa Xaa Xaa Xaa Xaa Xaa Xaa Xaa Xaa Xaa Xaa Xaa Xaa
370 375 380

Xaa Xaa Xaa Xaa Xaa Xaa Xaa Xaa Xaa Xaa Xaa Xaa Xaa Xaa Xaa Xaa
385 390 395 400

Xaa Xaa Xaa Xaa Xaa Xaa Xaa Xaa Xaa
405

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:HIV-1 reverse transcriptase (RT) catalytic site region sequence motif, wild-type RT (179-187), RT-WT

```
<400> SEQUENCE: 7

Val Ile Tyr Gln Tyr Met Asp Asp Leu
  1               5


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region,
      RT-1Y immunostimulating peptide

<400> SEQUENCE: 8

Tyr Ile Tyr Gln Tyr Met Asp Asp Leu
  1               5


<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:HIV-gag
      peptide, gag (p17) (77-85), p17-WT

<400> SEQUENCE: 9

Ser Leu Tyr Asn Thr Val Ala Thr Leu
  1               5


<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:Flu matrix
      peptide 58-66, FMP, Flu-MP (58-66)

<400> SEQUENCE: 10

Gly Ile Leu Gly Phe Val Phe Thr Leu
  1               5


<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:variant of
      synthetic sequence motif derived from HIV-1
      reverse transcriptase (RT) catalytic site region
      immunostimulating peptide
<220> FEATURE:
<221> NAME/KEY: MOD_RES
<222> LOCATION: (1)
<223> OTHER INFORMATION: Xaa = any hydrophobic amino acid, preferably
      Val

<400> SEQUENCE: 11

Xaa Leu Tyr Gln Tyr Met Asp Asp Val
  1               5


<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:RT
      (179-187)-WT alanine substituted peptide 1A
```

<400> SEQUENCE: 12

Ala Ile Tyr Gln Tyr Met Asp Asp Leu
1 5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:RT
(179-187)-WT alanine substituted peptide 2A

<400> SEQUENCE: 13

Val Ala Tyr Gln Tyr Met Asp Asp Leu
1 5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:RT
(179-187)-WT alanine substituted peptide 3A

<400> SEQUENCE: 14

Val Ile Ala Gln Tyr Met Asp Asp Leu
1 5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:RT
(179-187)-WT alanine substituted peptide 4A

<400> SEQUENCE: 15

Val Ile Tyr Ala Tyr Met Asp Asp Leu
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:RT
(179-187)-WT alanine substituted peptide 5A

<400> SEQUENCE: 16

Val Ile Tyr Gln Ala Met Asp Asp Leu
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:RT
(179-187)-WT alanine substituted peptide 6A

<400> SEQUENCE: 17

Val Ile Tyr Gln Tyr Ala Asp Asp Leu
1 5

<210> SEQ ID NO 18
<211> LENGTH: 9
<212> TYPE: PRT

```
<213> ORGANISM: Artificial Sequence
<220> FEATURE:
<223> OTHER INFORMATION: Description of Artificial Sequence:RT
      (179-187)-WT alanine substituted peptide 7A

<400> SEQUENCE: 18

Val Ile Tyr Gln Tyr Met Ala Asp Leu
  1               5


<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:RT
      (179-187)-WT alanine substituted peptide 8A

<400> SEQUENCE: 19

Val Ile Tyr Gln Tyr Met Asp Ala Leu
  1               5


<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:RT
      (179-187)-WT alanine substituted peptide 9A

<400> SEQUENCE: 20

Val Ile Tyr Gln Tyr Met Asp Asp Ala
  1               5


<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:RT
      (179-187)-WT substituted peptide 2L

<400> SEQUENCE: 21

Val Leu Tyr Gln Tyr Met Asp Asp Leu
  1               5


<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:RT
      (179-187)-WT substituted peptide 9V

<400> SEQUENCE: 22

Val Ile Tyr Gln Tyr Met Asp Asp Val
  1               5


<210> SEQ ID NO 23
<211> LENGTH: 408
<212> TYPE: PRT
<213> ORGANISM: Artificial Sequence
<220> FEATURE:
<223> OTHER INFORMATION: Description of Artificial Sequence:variant
      of synthetic sequence motif derived from HIV-1 reverse
      transcriptase (RT) catalytic site region, immunostimulating
      peptide, fusion molecule
<220> FEATURE:
<221> NAME/KEY: MOD_RES
<222> LOCATION: (1)..(200)
```

-continued

```
<223> OTHER INFORMATION: Xaa = any amino acid, may be present or absent
<220> FEATURE:
<221> NAME/KEY: MOD_RES
<222> LOCATION: (201)
<223> OTHER INFORMATION: Xaa = any hydrophobic amino acid
<220> FEATURE:
<221> NAME/KEY: MOD_RES
<222> LOCATION: (209)..(408)
<223> OTHER INFORMATION: Xaa = any amino acid, may be present or absent

<400> SEQUENCE: 23

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Tyr Gln Tyr Met Asp Asp Val
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
```

-continued

```
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa
                405
```

COMPOSITIONS COMPRISING NUCLEIC ACIDS ENCODING HIV-1 REVERSE TRANSCRIPTASE CTL EPITOPES

CROSS-REFERENCES TO RELATED APPLICATIONS

The present application claims priority to U.S. patent application Ser. No. 10/551,405, filed on Sep. 29, 2005, issued Jun. 8, 2010 as U.S. Pat. No. 7,731,971, which is a National Stage Application of PCT/US2004/009617, filed Mar. 29, 2004, which claims priority to U.S. Provisional Patent Application No. 60/459,507, filed on Mar. 31, 2003; the full disclosures of which are incorporated herein by reference.

FIELD OF THE INVENTION

The present invention relates to the fields of immunology and genetics, particularly with regard to HIV infection and prevention of the same. The present invention provides peptides and proteins for use in second generation HIV vaccines and as diagnostic tools in the treatment and control of HIV infection. The antiviral protection shown by compositions of the present invention has not been previously achieved with an HLA epitope-enhanced vaccine. These findings define a critical balance between MHC affinity and receptor crossreactivity required for effective epitope enhancement and also demonstrate construction and efficacy of such a component of a new generation vaccine.

BACKGROUND OF THE INVENTION

Protection by classical vaccines such as polio vaccine is mediated mostly by neutralizing antibodies, but such antibody-inducing vaccines have been ineffective against viruses causing chronic infection such as HIV or hepatitis C virus. Rather, in this case, T-cell immunity might be crucial as has been confirmed by CD8 cell depletion in AIDS virus infection of macaques (Schmitz, J. E., M. et al., (1999), Science 283: 857; and Jin, X., et al., (1999), J. Exp. Med. 189:991her, viral sequences evolving under immune selective pressure would not likely have optimal HLA molecule-binding epitopes. Thus, modifying epitope sequence to improve the CTL response could be one effective strategy toward development of new generations of vaccines (Berzofsky, J. A., et al., (1999) Immunol. Rev. 170:151; and Berzofsky, J. A., et al., (2001) Nature Reviews Immunology 1:209).

CD8 cytotoxic T cells (CTL) play a major role in protection against HIV or SW virus (Musey, L., J. et al., (1997) N Engl J Med 337:1267; Schmitz, J. E., et al., (1999), Science 283: 857; and Jin, X., et al., (1999), J. Exp. Med. 189:991.). Nevertheless, the natural immune response to HIV is often unable to clear the infection. Although a number of antigens that induce CTL responses and can help to eliminate or reduce virus production by killing viral producer cells have been reported so far, these do not seem to be sufficient to eliminate infection in most cases. There is no reason to expect that the HIV sequence would have evolved to have optimal CTL epitopes to allow eradication of the virus.

We have previously succeeded in improving the affinity of a hepatitis C core epitope for HLA-A2.1 (Sarobe, P., et al., (1998), J. Clin. Invest. 102:1239) and of a helper epitope for murine class II MHC (Ahlers, J. D., et al., (1997), Proc. Natl. Acad. Sci. U.S.A. 94:10856; and Ahlers, J. D., et al., (2001), J. Clin. Invest. 108:1677), and an epitope-enhanced melanoma peptide has shown efficacy in human clinical trials (Rosenberg, S. A., et al., (1998) Nature Medicine 4:321). Other complementary approaches to improve affinity for T-cell receptors have been devised (Zaremba, S., et al., (1997) Cancer Res 57:4570; and Slansky, J. E., et al., (2000) Immunity 13:529; and Tangri, S., et al., (2001) J Exp Med 194:833). Although one substitution resulting in higher affinity HLA binding of another HIV peptide has been reported (Pogue, R. R., I. et al., (1995) Proc. Natl. Acad. Sci. U.S.A. 92:8166), no systematic attempt to improve epitopes of HIV has been carried out. In particular, no systematic analysis of the competing effects of substitutions on HIV peptide binding to the HLA class I molecule vs peptide/HLA complex binding to the T cell receptor has been reported.

Further, to our knowledge, protection against viral infection in vivo by an epitope-enhanced vaccine mediated by CTL restricted by a human HLA molecule has not previously been demonstrated.

SUMMARY OF THE INVENTION

In principle it should be possible to improve the immunogenicity of epitopes, a process called "epitope enhancement," to develop a more highly effective HIV vaccine (Berzofsky, J. A., et al., (1999), Immunol. Rev. 170:151; and Berzofsky, J. A., et al., (2001), Nature Reviews Immunology 1:209). Using epitope enhancement, we have developed non-natural peptides and proteins having utility as the active agents in second generation vaccines and as diagnostic tools in the treatment and prevention of HIV-1 infection. The present invention also includes methods for using these vaccines and reagents.

Accordingly, the present invention provides immunostimulating peptides having an amino acid sequence $X_1$LYQYMDDV (SEQ ID NO:1), where $X_1$ is any hydrophobic amino acid. This amino acid sequence motif, which to our knowledge is not found in nature, is common to all peptides and proteins of the invention, and preferably has the amino acid sequence VLYQYMDDV (SEQ ID NO:2) or YLYQYMDDV (SEQ ID NO:3).

As noted above, immunostimulating proteins are also provided by the present invention, for example, one embodiment provides an immunostimulating peptide or protein comprising the sequence $X_1X_2$LYQYMDDV$X_3$ (SEQ ID NO:4) where $X_1$ is a sequence of amino acid residues of between 0 and 200 residues in length; $X_2$ is any hydrophobic amino acid; and, $X_3$ is a sequence of amino acid residues of between 0 and 200 residues in length. Preferably, these immunostimulating proteins have the sequence $X_1$VLYQYMDDV$X_3$ (SEQ ID NO:5), or $X_1$YLYQYMDDV$X_3$ (SEQ ID NO:6).

A further embodiment provides proteins and fusion molecules having the amino acid sequence motif $X_1$LYQYMDDV (SEQ ID NO:1), where $X_1$ is any hydrophobic amino acid. The fusion molecules may include, for example, HIV-1 viral proteins, glycolipid conjugates, or conjugation of a protein or peptide having the $X_1$LYQYMDDV (SEQ ID NO:1) sequence motif with an immunostimulating carrier protein, as described herein. In some embodiments, the fusion molecules include repeat ("concatameric") $X_1$LYQYMDDV (SEQ ID NO:1) sequences. Concatamers of the present invention are particularly efficient both as protein/peptide antigens and, when provided as encoding nucleic acid sequences, gene therapy reagents, as described herein.

All peptides, proteins and fusion molecules of the present invention may be modified as described herein. Modifications may be made for a variety of reasons, for example, to increase solubility, cell uptake, or ease administration as a medicament. Modifications contemplated as being encompassed by the invention include N-terminal acetylation of peptides, C-terminal amidation, esterification and reduction of the C-terminal amino acid carboxyl group; and glycosylation, amidation, acylation, esterification, oxidation or rediction of aminoacyl side chain residues, as is known in the art. (see, e.g., Techniques in Protein Modification and Analysis pp. 151-154, 1995).

The present invention also provides immunostimulating peptides and proteins in medicament form. These embodiments contain, at a minimum, a therapeutically effective amount of one or more of the immunostimulating peptides and proteins discussed above, with a pharmaceutically acceptable excipient. Exemplary excipients are discussed in detail, below. The medicaments may optionally include immunostimulant(s) to further enhance their therapeutic value.

Other medicaments provided by the invention include an immunostimulating peptide or protein, or a nucleic acid encoding the same, pulsed or transduced into dendritic cells.

Nucleic acid vaccines, including "live" vaccines are also contemplated by the present invention. For example, the invention provides medicaments that contain vector(s) having a nucleic acid that includes a nucleotide sequence encoding one of the immunostimulatory peptides or proteins discussed above. Some of the vectors of the present invention may include coding nucleotide sequences for more than one of the immunostimulating peptides and proteins, including transcriptional units for producing more than one of the immunostimulating peptides and proteins by, for example placing an IRES sequence before downstream coding sequences. Methods for forming constructs of this type are well known to those of skill in the art.

Introducing a nucleic acid vaccine of the present invention to a subject results in expression of the nucleic acid, thereby inducing an immune response in the subject directed against an epitope of a product(s) encoded by the nucleic acid.

Nucleic acid medicaments of the present invention include naked nucleic acids, virus and bacterial vectors. Construction and delivery methods for these types of vaccines are known. (see, e.g., U.S. Pat. Nos. 6,534,483; 6,495,318; 6,475,995; Drobnitz, J., Advanced Drug Delivery Reviews, vol. 3, 229-245, 1989; Kuo, P. Y. P. et al., Critical Reviews in Eukaryotic Gene Expression, vol. 6, No. 1, pp. 59-73, 1996; Hopkins et al. Infect Immun. 63:3279-3286, 1995; Srinavasin et al. Vaccines 95, R. N. Chanock et al., Eds., Cold Spring Harbor Laboratory Press, Plainview, N.Y., p 273-280, 1995).

Another embodiment of the invention are methods for preventing or treating an HIV-1 infection that entail administering a dose of the medicament discussed above in an amount effective to induce an immune response capable of preventing HIV-1 infection or reducing HIV-1 viral load in a patient. These medicaments are particularly suited for use in primates, including humans.

An additional embodiment is methods of assessing immune function or diagnosing exposure to HIV-1 for a subject. Performing these methods involves, at a minimum, contacting a blood sample, including T cells, obtained from the subject cells with a peptide or protein of the present invention, then determining an immune response of the subject's T cells to the peptide or protein. In some aspects, the determining step is performed by assaying for RANTES or IFN-g production, or lysis of cells displaying the peptide by cytotoxic T lymphocytes, or any combination of the three parameters, induced with the peptide.

DEFINITIONS

Figure 1:
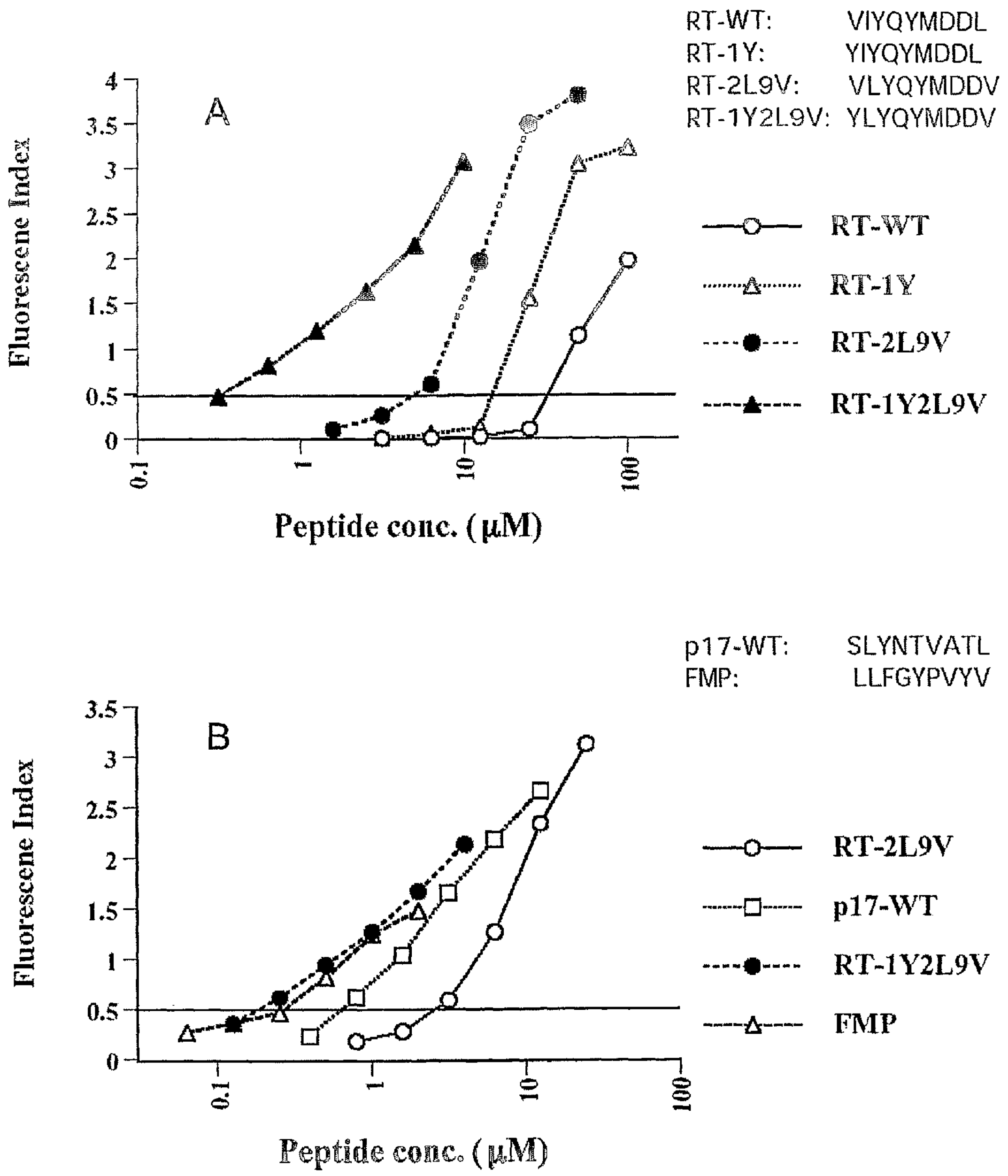
FIG. 1A is a comparison of the HLA-A2 binding curves among the wild type RT (179-187), VIYQYMDDL (SEQ ID NO:7), RT-1Y (YIYQYMDDL; SEQ ID NO:8), RT-2L9V (VLYQYMDDV; SEQ ID NO:2), and RT-1Y2L9V (YLYQYMDDV; SEQ ID NO:3) in the T2-binding assay.
FIG. 1B is a comparison of the HLA-A2 binding curves among the RT-2L9V, p17-WT (SLYNTVATL; SEQ ID NO:9), RT-1Y2L9V and FMP (GILGFVFTL; SEQ ID NO:10).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The terms "peptide" and "protein" are used herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. Peptides and proteins of the present invention include amino acid polymers having D- and L-isoforms of individual amino acid residues, as well as other amino acid variants, as described herein. Peptides are distinguished by the number of amino acid residues making up the primary structure of the molecule. For purposes of this invention, peptides are those molecules comprising up to 50 amino acid residues, and proteins comprise 50 or more amino acid residues. However, methods of synthesis and/or delivery of peptides and proteins of the invention are similar, if not identical, as will be appreciated by one of skill in the art. Therefore, where appropriate, these terms are synonymous when discussing methods of synthesis, modification or use as therapeutic or diagnostic reagents.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. "Amino acid analog" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-TUB Biochemical Nomenclature Commission. Nucleotides, likewise, may be referred to by their commonly accepted single-letter codes.

"Amino acid sequence" refers to the positional relationship of amino acid residues as they exist in a given polypeptide or protein.

"Hydrophobic amino acid" refers to amino acids, both natural and synthetic, having a hydrophobicity value of 0.5 or greater. Hydrophobicity values are "scaled" values from computational log(P) determinations by the "Small Fragment Approach" (see, "Development of Hydrophobicity Parameters to Analyze Proteins Which Bear Post- or Cotranslational Modifications" Black, S. D. and Mould, D. R. (1991) Anal. Biochem. 193, 72-82). The equation used to scale raw log(P) values to the scaled values given is as follows: Scaled Parameters=(Raw Parameters+2.061)/4.484.

Hydrophobicity values for naturally occurring amino acids are given in table 1, below.

TABLE 1

Designations for Unmodified L-alpha-Amino Acids

| Amino Acid | 3-Letter Code | 1-Letter Code | Hydrophobicity |
|---|---|---|---|
| Alanine | Ala | A | 0.616 |
| Cysteine | Cys | C | 0.680 |
| Aspartate | Asp | D | 0.028 |
| Glutamate | Glu | E | 0.043 |
| Phenylalanine | Phe | F | 1.00 |
| Glycine | Gly | G | 0.501 |
| Histidine | His | H | 0.165 |
| Isoleucine | Ile | I | 0.943 |
| Lysine | Lys | K | 0.283 |
| Leucine | Leu | L | 0.943 |
| Methionine | Met | M | 0.738 |
| Asparagine | Asn | N | 0.236 |
| Proline | Pro | P | 0.711 |
| Glutamine | Gln | Q | 0.251 |
| Arginine | Arg | R | 0.000 |
| Serine | Ser | S | 0.359 |
| Threonine | The | T | 0.450 |
| Valine | Val | V | 0.825 |
| Tryptophan | Trp | W | 0.878 |
| Tyrosine | Tyr | Y | 0.880 |

"Aliphatic amino acid" refers to amino acids, both natural and synthetic, having a hydrophobicity value of 0.5 or greater, and only saturated carbon-carbon bonds. Aliphatic amino acids include alanine, glycine, isoleucine, leucine, proline and valine.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-o-methyl ribonucleotides and peptide-nucleic acids (PNAs).

Unless otherwise indicated, a particular nucleic acid sequence also implicitly encompasses conservatively modified variants thereof (e.g., degenerate codon substitutions, see below) and complementary sequences, as well as the sequence explicitly indicated.

"Conservatively modified variants" refers to those nucleic acids that encode identical or essentially identical amino acid sequences, or where the nucleic acid does not encode an amino acid sequence, to essentially identical sequences. The term also refers to fragments of particular sequences, where the sequence of the fragment has been conservatively modified as described herein. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and UGG, which is ordinarily the only codon for tryptophan) can be modified to yield a functionally identical molecule. Accordingly, each silent variation of a nucleic acid that encodes a polypeptide is implicit in each described sequence. (See e.g., Batzer et al., Nucleic Acid Res., 19:5081 (1991); Ohtsuka et al., S. Biol. Chem., 260:2605-2608 (1985); Rossolini et al., Mol. Cell. Probes, 8:91-98 (1994)).

The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein or anti-sense strand.

"Excipient" refers to an inert substance used as a diluent or vehicle for a drug "Immunostimulant", and grammatical variants thereof, refer to any substance capable of stimulating an immune response.

An "immune response" is any physiological change resulting in activation and/or expansion of a "B" cell population with production of antibodies, and/or activation and/or expansion of a "T" cell population.

"T cell" refers to any lymphocyte that matures in the thymus and has the ability to recognize specific peptide antigens, or specific peptide antigens complexed with a major histocompatibility complex protein (MHC), through the receptors on its cell surface.

"Vector" refers to any type of genetic construct containing a nucleic acid capable of being transcribed in a cell. Vectors used for the amplification of nucleotide sequences (both coding and non-coding) are also encompassed by the definition. In addition to the coding sequence, vectors will generally include restriction enzyme cleavage sites and the other initial, terminal and intermediate DNA sequences that are usually employed in vectors to facilitate their construction and use. The expression vector can be part of a plasmid, virus, or nucleic acid fragment.

"Fusion molecules" refers to any molecule formed through the structural linkage of a peptide of the present invention to one or more molecules, particularly macromolecules. In the context of the present invention other molecules that can be joined to peptides of the invention to form fusion molecules include sugars and polysaccarides, other peptides and proteins, lipids, and nucleotides and nucleic acids.

"HIV-1 infection" refers to indications of the presence of the HIV-1 virus in an individual including asymptomatic seropositivity, aids-related complex (arc), and acquired immunodeficiency syndrome (AIDS).

"HIV-1 viral load" refers to the number of viral particles in a sample of blood plasma. HIV viral load is increasingly employed as a surrogate marker for disease progression. It is measured by PCR and bDNA tests and is expressed in number of HIV copies or equivalents per milliliter.

"IFN-γ" or "interferon-γ" refers to a cytokine elaborated by T lymphocytes in response to either specific antigen or mitogenic stimulation.

DETAILED DESCRIPTION

I. Introduction

The present invention provides immunostimulatory peptides and proteins, and the nucleic acids encoding them, for use as therapeutic and diagnostic tools for the treatment of HIV infection. The peptides and proteins of the invention all share the same amino acid sequence motif, which is a variant of a synthetic sequence motif derived from the HIV-1 reverse transcriptase catalytic site region. This motif has the sequence $X_1$LYQYMDDV (SEQ ID NO:1), where $X_1$ is any hydrophobic amino acid.

The invention also provides second generation HIV vaccines and methods for their use. These vaccines have the immunostimulatory peptides and proteins of the invention, or the nucleic acids encoding them, as their active ingredients.

The peptides and nucleic acids of the present invention may also be used as diagnostic reagents for determining the presence or monitoring the progression of an HIV infection. For example, the nucleic acids of the present invention may be labeled with a detectable label, such as a fluorescent or radioactive moiety and used as a hybridization probe to detect the presence of HIV nucleic acid in a body fluid of an infected individual. Failure to detect hybridization partners for such probes would be indicative of absence of infection. Peptides and proteins of the invention may for example be used to test for an immune response against the peptide or protein, as described herein.

As shown by the examples to this application, peptides of the present invention produce high avidity CTL. As high avidity CTL have been found to be critical in clearance of virus infection (Alexander-Miller, M. A., et al., (1996), *Proc. Natl. Acad. Sci. U.S.A.* 93:410; and Gallimore, A., T. et al., (1998), *J Exp Med.* 187:1647) the ability of an epitope-enhanced peptide to induce high avidity CTL, as we have seen here and with a hepatitis C virus peptide (Sarobe, P., C. D. et al., (1998), *J. Clin. Invest.* 102:1239.), makes the molecules of the present invention attractive as vaccines. These molecules are applicable to all forms of vaccine, e.g., peptide, DNA, recombinant viral or bacterial vector, or live attenuated virus. They also define and demonstrate the efficacy of a prototype conserved enhanced epitope that can be incorporated into many candidate vaccines currently under study.

II. Producing Immunostimulatory Peptides

The present invention provides immunostimulating peptides with the amino acid sequence $X_1$LYQYMDDV (SEQ ID NO:11), where $X_1$ is any hydrophobic amino acid, preferably valine. These immunostimulatory peptides may be synthesized by any of the techniques that are known to those skilled in the peptide art, including recombinant DNA techniques and isolated natural sources, such as whole viruses or tumors, which express proteins that include a segment having the amino acid sequence of the present invention.

Synthetic chemistry techniques, such as a solid-phase Merrifield-type synthesis, are preferred for reasons of purity, antigenic specificity, freedom from undesired side products, ease of production and the like. Excellent summaries of the many techniques available can be found in J. M. Steward & J. D. Young, SOLID PHASE PEPTIDE SYNTHESIS, W.H. Freeman Co., San Francisco, (1969); M. Bodanszky et al., PEPTIDE SYNTHESIS, John Wiley & Sons, Second Edition, (1976); and J. Meienhofer, HORMONAL PROTEINS AND PEPTIDES, Vol. 2, p. 46, Academic Press, New York (1983) for solid phase peptide synthesis, and E. Schroder & K. Kubke, 1 THE PEPTIDES, Academic Press, New York (1965) for classical solution synthesis, each being hereby incorporated herein by reference. Appropriate protective groups usable in such synthesis are described in the above texts and in J. F. W. McOmie, PROTECTIVE GROUPS IN ORGANIC CHEMISTRY, Plenum Press, New York (1973), the entire disclosure of which is also incorporated herein by reference. Simplified methods for solid phase synthesis of peptides on a small scale also are known. See for instance, Houghten, R. A., Proc. Natl. Acad. Sci. U.S.A. 82:5131-5135 (1985); and Houghton, M., Q.-L. Choo, & G. Kuo, European Patent Application 88310922 (1988).

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., Molecular Cloning, A Laboratory Manual, Cold Spring Harbor Press, Cold Spring Harbor, N.Y. (1982), which is incorporated herein by reference.

Coding sequences for the immunostimulatory peptides and proteins of the present invention may be synthesized by chemical techniques, for example, the phosphotriester method of Matteucci et al., J. Am. Chem. Soc. 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the immunostimulatory peptide or protein. A number of such vectors and suitable host systems are now available. For expression, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

III. Producing Fusion Molecules Having an Immunostimulatory Amino Acid Sequence Although the peptides of the invention will preferably be substantially free of contaminants, including naturally occurring host cell proteins and fragments thereof, in some embodiments the peptides can be synthetically conjugated to native fragments or particles, immunostimulatory molecules and the like to form advantageous fusion molecules. Both peptides and fusion molecules of the invention may be in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

One fusion molecule embodiment is a peptide or protein that includes in its amino acid sequence the sequence motif $X_1X_2$YQYMDDV$X_3$ (SEQ ID NO:4), where $X_1$ is a sequence of amino acid residues of between 0 and 200 residues in length; $X_2$ is any hydrophobic amino acid; and, $X_3$ is a second sequence of amino acid residues of between 0 and 200 residues in length that may be different from the $X_1$ sequence.

Another fusion molecule embodiment of the invention can be a glycoprotein, lipoprotein, nucleoprotein or other heterologous molecule having the sequence motif $X_1$LYQYMDDV (SEQ ID NO:1), where $X_1$ is any hydrophobic amino acid. Preferably this fusion protein will include an amino acid sequence for an HIV-1 viral protein or an immunostimulating carrier protein.

These fusion molecules may be produced by methods known to those of skill in the art and are typically designed to improve antigenicity of the immunostimulatory peptide sequence included in the molecule, or aid in its delivery to a patient. Thus the peptides and fusion molecules of the present invention may be modified as necessary to provide certain desired attributes, e.g., improved pharmacological characteristics, while increasing or at least retaining substantially all of the biological activity of the unmodified peptide to bind the desired MHC molecule and induce a CTL response.

For instance, the fusion molecules may be subject to various changes, such as substitutions, either conservative or nonconservative, where such changes might provide for certain advantages in their use, such as improved MHC binding. By conservative substitutions is meant replacing an amino acid residue with another that is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, Science 232:341-347 (1986), Barany and Merrifield, The Peptides, Gross and Meienhofer, eds. (New York, Academic Press), pp. 1-284 (1979); and Stewart and Young, Solid Phase Peptide Synthesis, (Rockford, Ill., Pierce), 2d Ed. (1984), incorporated by reference herein.

The peptides of the invention may also be modified by extending their amino acid sequence, e.g., by the addition of amino acids to their N or C terminus. The peptides or fusion molecules of the invention can also be modified by altering the order or composition of certain residues, it being readily appreciated that the core immunostimulatory sequence, $X_1$LYQYMDDV (SEQ ID NO:1), may generally not be altered without an adverse effect on biological activity. The noncritical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Fusion molecules may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, peptides and Proteins, Vol. VII (Weinstein ed., 1983).

Modifications of fusion molecules with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides of the present invention may be modified to provide desired attributes other than improved serum half life. For example, the ability of the peptides to induce CTL activity can be enhanced by linkage to a sequence that contains at least one epitope capable of inducing a T helper cell response. Particularly preferred immunostimulatory peptides/T helper conjugates are linked together by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the immunostimulatory peptide may be linked to the T helper peptide without a spacer. Linkage to the T helper peptide may be at the amino or carboxy terminus of the immunostimulatory peptide. The amino terminus of either the immunostimulatory peptide or the T helper peptide may be acylated. The carbotyl terminus of either the immunostimulatory peptide or the T helper peptide may also be modified, e.g., by amidation, esterification or reduction of the carboxyl group. Methods for performing these modifications are well known to those of skill in the art.

In some embodiments of the invention it may, for example, be desirable to include in the pharmaceutical compositions of the invention at least one component which assists in priming a CTL response. Lipids have been identified as agents capable of assisting the priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunostimulatory peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunostimulatory peptide. As another example of lipid priming of CTL responses, *E. coli* lipoproteins, such as tripalmitoyl-S-glycerylcysteinly-seryl-serine ($P_3$ CSS) can be used to prime virus specific CTL when covalently attached to an appropriate peptide. See, Deres et al., Nature 342:561-564 (1989), incorporated herein by reference. Immunostimulatory peptides of the invention can be coupled to $P_3$ CSS, for example, and the lipopeptide administered to an individual to specifically prime a CTL response to the target antigen. Further, as the induction of neutralizing antibodies can also be primed with $P_3$ CSS conjugated to a peptide that displays an appropriate epitope, the two compositions can be combined to more effectively elicit both humoral and cell-mediated responses to infection.

The peptides of this invention are thought to have utility for a vaccine to prevent HCV infection or for therapeutic purposes in individuals infected with HCV. For example, the peptides can be used by themselves, or they can be used to prepare immunogenic conjugates in which a peptide is conjugated to an agent which provokes an immune response to a complex comprising the conjugated peptide bound to a carrier protein, according to methods known in the art. See, for instance, M. F. Good, Science 235:1059-1062 (1987); and Palker, T. J., J. Imm. 142:3612-3619 (1989). Agents which can be conjugated to peptides to provoke an immune response include toxoids such as diphtheria toxoid or tetanus toxoids, which are commonly recognized by the body (of immunized persons) and eliminated by the immune system. Alternatively, a gene sequence encoding the peptide may be incorporated into a recombinant gene and expressed as part of a vector, for instance, a recombinant virus such as vaccinia virus made by the method of Chakrabarti, S., et al., Nature 320:535-537 (1986).

The peptide of the present invention also may be incorporated into a larger peptide comprising additional epitopes, either other T cell epitopes or B cell epitopes. Thus, the peptide may be used as part of a multivalent vaccine which induces cytotoxic T cell responses to multiple epitopes of HCV or of HCV and another virus. In addition, the multivalent vaccine peptide may include helper T cell epitopes and B cell epitopes of HCV or another virus, to effect induction of an antibody response as well as a cytotoxic T cell response. For instance, one could attach a helper T cell epitope from HIV, such as those described in Cease K. B., et al., Proc. Natl. Acad. Sci. USA 84:4249-4253 (1987), to provide T cell help for the CTL response. Also see Berzofsky, J. A., et al., J. Clin. Invest. 88:876-884 (1991); for peptides generating antiviral cytotoxic T lymphocytes, Hart, M. K., et al., Proc Natl Acad Sci USA 88:9448-9452 (1991); and for peptides inducing an antibody response, Hart M., K., et al., J. Immunol. 145:2677-2685 (1990). Collett, N. S., V. Moennig, and M. C. Horzinek. 1989. Recent advances in pestivirus research. 3. Gen. Virol. 70:253-266.

Those skilled in the art of preparing pharmaceutical compositions will realize how to prepare the peptides and conjugates described above for pharmaceutical use in composition comprising accepted pharmaceutical carriers.

IV. Methods for Assessing an Immune Response Against HIV-1

The peptides also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

An important aspect to the diagnosis and treatment of HIV-1 is a determination of the presence of viral infection, and when infection is present, monitoring the viral load or the infected individual. The present invention addresses these issues by providing methods of assessing immune function or diagnosing exposure to HIV-1 for a subject. Performing the methods involves contacting a blood sample from the subject that contains T cells with an immunostimulatory peptide of the present invention; and, determining if peptide contact induces an immune response, preferably a CTL response. The blood sample will need to contain antigen-presenting cells. These cells may be endogenous to the sample, or added from an external source. Antigen-presenting cells can be normal cells such as peripheral blood mononuclear cells or dendritic cells (Inaba, et al., J. Exp. Med. 166:182 (1987); and Boog, Eur. J. Immunol. 18:219 [1988]).

Next, peptides that test positive in the MHC class I binding assay are assayed for the ability of the peptides to induce specific CTL responses in vitro. For instance, antigen-presenting cells that have been incubated with a peptide can be assayed for the ability to induce CTL responses in responder cell populations.

Alternatively, mutant mammalian cell lines that are deficient in their ability to load class I molecules with internally processed peptides, such as the mouse cell lines RMA-S (Karre, et al. Nature, 319:675 (1986); Ljunggren, et al., Eur. J. Immunol. 21:2963-2970 (1991)), and the human somatic T cell hybridoma, T-2 (Cerundolo, et al., Nature 345:449-452 (1990)) and that have been transfected with the appropriate human class I genes may be conveniently used. To test for the capacity of an immunostimulatory peptide of the invention to induce in vitro primary CTL response, the peptide is added to the cells. Other eukaryotic cell lines which could be used include various insect cell lines such as mosquito larvae (ATCC cell lines CCL 125, 126, 1660, 1591, 6585, 6586), silkworm (ATTC CRL 8851), armyworm. (ATCC CRL 1711), moth (ATCC CCL 80) and *Drosophila* cell lines such as a Schneider cell line (see Schneider J. Embryol. Exp. Morphol. 27:353-365 [1927]). That have been transfected with the appropriate human class I MHC allele encoding genes and the human $B_2$ microglobulin genes.

Alternatively, IFN-γ and/or RANTES production by stimulated T cells can be measured in the T cell culture supernatant. Methods for measuring CTL response, RANTES and IFN-γ production of stimulated T cells are well known in the art, some of which are discussed in the general methods of the examples section, below and elsewhere in this specification.

The immunogenic peptides of this invention may also be used to make monoclonal antibodies. Such antibodies may be useful as potential diagnostic or therapeutic agents.

V. Vaccines for Immunizing Against HIV-1

The peptides of the present invention and pharmaceutical and vaccine compositions thereof are useful for administration to mammals, particularly humans, to treat and/or prevent viral infection and cancer. Examples of diseases which can be treated using the immunogenic peptides of the invention include indications of the presence of the HIV-1 virus in an individual including asymptomatic seropositivity, aids-related complex (arc), and acquired immunodeficiency syndrome (AIDS).

Pharmaceutical compositions of the immunostimulatory peptides of the invention are administered to an individual already suffering from indications of the presence of the HIV-1 virus including asymptomatic seropositivity, aids-related complex (arc), and acquired immunodeficiency syndrome (AIDS). Those in the incubation phase or the acute phase of infection can be treated with the immunogenic peptides separately or in conjunction with other treatments, as appropriate. In therapeutic applications, compositions are administered to a patient in an amount sufficient to elicit an effective immune response, preferably a CTL response to the virus and cure, or at least partially arrest symptoms and/or complications. An amount adequate to accomplish this is defined as "therapeutically effective dose." Amounts effective for this use will depend on, e.g., the peptide and/or protein composition, the manner of administration, the stage and severity of the disease being treated, the weight and general state of health of the patient, and the judgment of the prescribing physician, but generally range for the initial immunization (that is for therapeutic or prophylactic administration) from about 0.001 to about 200 mg/kg, more preferably about 0.01 to about 100 mg/kg, most preferably about 0.1 to 50 mg/kg peptide, followed by boosting dosages of from about 0.001 to about 100 mg/kg, more preferably about 0.01 to about 50 mg/kg peptide pursuant to a boosting regimen over weeks to months, depending upon the patient's response and condition determined by measuring specific CTL activity in the patient's blood as described previously and in the examples that follow.

It should be kept in mind that the peptides and compositions of the present invention may generally be employed individuals with chronic HIV infections, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions:

For therapeutic use, administration should begin at the first sign of viral infection. This is followed by boosting doses until at least symptoms are substantially abated and for a period thereafter. Loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the infection. Where susceptible individuals are identified prior to or during infection the composition can be targeted to them, minimizing need for administration to a larger population.

The peptide compositions may also be used to stimulate the immune system to eliminate virus-infected cells in carriers. It is important to provide an amount of immuno-potentiating peptide in a formulation and mode of administration sufficient to effectively stimulate a cytotoxic T cell response. Thus, in these cases, a representative dose is in the range of about 0.001 to about 200 mg/kg, more preferably about 0.01 to about 100 mg/kg, most preferably about 0.1 to 50 mg/kg peptide per dose. Immunizing doses followed by boosting doses at established intervals, e.g., from one to four weeks, may be required, possibly for a prolonged period of time to effectively immunize an individual. Administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in a pharmaceutically acceptable excipient, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of immunostimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

Both peptides and the nucleic acids encoding them of the invention may also be administered via liposomes. Liposomes are useful in increasing the half-life of the peptides. Liposomes include emulsions, foams, micelles, insoluble monolayers, liquid crystals, phospholipid dispersions, lamellar layers and the like. In liposome preparations the peptide to be delivered may be incorporated as part of a liposome, alone or in conjunction with a molecule that binds to, e.g., a receptor prevalent among lymphoid cells, such as monoclonal antibodies that bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728, 4,837,028, and 5,019,369, incorporated herein by reference.

For targeting to immune cells, a ligand to be incorporated into the liposome can include, e.g., antibodies or fragments thereof specific for cell surface determinants of the desired immune system cells. A liposome suspension containing an immunostimulatory peptide may be administered intravenously, locally, topically, etc. in a dose which varies according to, inter alia, the manner of administration, the peptide being delivered, and the stage of the disease being treated.

For solid compositions, conventional nontoxic solid carriers may be used including, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 10% to about 95% of active ingredient, that is, one or more peptides of the invention, and more preferably at a concentration of about 25% to about 75%.

For aerosol administration, the immunogenic peptides are preferably supplied in finely divided form along with a surfactant and propellant. Typical percentages of peptides are 0.01%-20% by weight, preferably 1%-10%. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

Another aspect the present invention is directed to vaccines that contain as an active ingredient an immunogenically effective amount of an immunostimulatory peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of HIV virus. Useful carriers are well known in the art, and include, e.g., thyroglobulin, albumins such as bovine serum albumin, tetanus toxoid, polyamino acids such as poly(lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. As mentioned above, CTL responses can be primed by conjugating peptides of the invention to lipids, such as $P_3$ CSS. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the peptides, and nucleic acids encoding them, of the invention are administered to a patient susceptible to or otherwise at risk of HIV infection, to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 0.001 to about 200 mg/kg, more preferably about 0.01 to about 100 mg/kg, most preferably about 0.1 to 50 mg/kg peptide, more commonly from about 0.01 to about 100 mg/kg, more preferably about 0.1 to 50 mg/kg peptide/body weight.

In some instances it may be desirable to combine the peptide vaccines of the invention with vaccines which induce neutralizing antibody responses to HIV-1, particularly to viral envelope antigens.

Immunostimulatory peptides may also be used to elicit CTL ex vivo, as well. The resulting CTL, can be used to treat patients that do not respond to other conventional forms of therapy, or will not respond to a peptide vaccine approach of therapy. See, e.g., U.S. Pat. No. 6,037,135 for methods of performing ex vivo CTL therapy. Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

Peptides and proteins of the present invention may also be used to pulse autologous dendritic cells as a means of immunization against the peptide.

Live Vaccines

For therapeutic or immunization purposes, the peptides of the invention can also be expressed by attenuated viral hosts, such as vaccinia or fowlpox. This approach involves the use of the virus as a vector to express nucleotide sequences that encode the peptides of the invention. Upon introduction into an infected host or uninfected host, the recombinant virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (Nature 351:456.460 (1991)). A wide variety of other vectors useful for therapeutic administration or immunization of the peptides of the invention, e.g., *Salmonella typhi* vectors and the like, will be apparent to those skilled in the art from the description herein.

Gene Therapy

Delivery into a patient of nucleic acids encoding peptides and proteins of the present invention may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

For example, the nucleic acid sequences may directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zifistra et al., Nature 342:435-438 (1989)).

Nucleic acids of the present invention may also serve as effective vaccines, by introducing them into suitable cells where they will be expressed and either secreted, or displayed on the cell surface of the transformed cell. For example nucleic acids encoding peptides and proteins of the present invention them may be used to transduce dendritic cells, which in turn can be used as vaccines for immunization.

Other modes of gene therapy are also contemplated by the present invention. For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5): 155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

General Methods

The following methods are general to all examples that follow. The inventors wish to thank Dr. Linda Sherman of the Scripps Research Institute, La Jolla, Calif., for kindly donating the Jurkat-A2K$^b$ cell line, A2 Kb mice. The inventors would also like to thank Dr. Bernard Moss, NIAID, for his gift of HIV reverse transcriptase (vCF21) or β-galactosidase (vSC8) and Dr. Victor Engelhard of the University of Virginia for his donation of a C1R.AAD cell line.

Synthetic Peptides

Peptides were prepared in an automated multiple peptide synthesizer (Symphony; Protein Technologies, Inc.) using Fmoc chemistry. Peptides were purified by reverse-phase HPLC, and their sequences confirmed on an automated sequencer (477A; Applied Biosystems, Foster City, Calif.). Some peptides were purchased from Multiple Peptide Systems (San Diego, Calif.).

Cells

A Jurkat-A2K$^b$ cell line was transfected with an HLA chimeric molecule containing α1 and α2 domains from human HLA-A2.1 and an α3 domain from mouse H-2K$^b$. A C1R.AAD cell line (HMYC1R transfected with an HLA chimeric molecule containing α1 and α2 domains from human HLA-A2.1 and an α3 domain from mouse H-2D$^d$) (Sarobe, P. et al., J. Clin. Invest. 102:1239). Cell lines were maintained in 10% FCS RPMI containing 1 mM sodium pyruvate, nonessential amino acids (Biofluid, Rockville, Md.), 4 mM glutamine, 100 U/ml penicillin, 100 μg/ml streptomycin, and 50 μM 2-mercaptoethanol.

Mice

Transgenic A2 Kb mice (Vitiello, et al., *J. Exp. Med.* 173: 1007) and transgenic HHD-2 mice (Pascolo, et al., *J. Exp. Med.* 185:2043; and Firat, H., S., et al., Eur J Immunol 31:3064.) were bred in our colony at BioCon Inc. (Rockville, Md.). A2 Kb mice express a chimeric HLA-A2.1 molecule with the α3 domain derived from the murine H-2K$^b$. HHD-2 mice have murine β2-microglobulin and murine H-2D$^b$ genes knocked out. HHD-2 mice are also transgenic for a human HLA-A2.1 that has a covalently-linked human β2-microglobulin and a murine D$^b$-derived α3 domain, which allows interaction with mouse CD8. Because of these genetic alterations, the only class I MHC molecule expressed by HHD-2 mice is human HLA-A2.1. The genetic changes to both mice allow for better binding of murine CD8. Both strains are on a C57BL/6 background.

T2 Binding Assay

Peptide binding to HLA molecules was measured using the T2 mutant cell line as described (Sarobe, P. et al., J. Clin. Invest. 102:1239; and Nijman, H. W., J., et al., Eur. J. Immunol. 23:1215.). Briefly, T2 cells ($3\times10^5$/well) were incubated overnight in 96-well plates with culture medium (a 1:1 mixture of RPMI 1640/EHAA containing 2.5% FBS, 100 U/ml penicillin, 100 μg/ml streptomycin) with 10 μg/ml human β2-microglobulin (Sigma Chemical Co., St. Louis, Mo.) and different peptide concentrations. The next day, cells were washed twice with cold PBS containing 2% FBS and incubated for 30 min at 4° C. with anti-HLA-A2.1 BB7.2 mAb (1/100 dilution of hybridoma supernatant) and 5 μg/ml FITC-labelled goat anti-mouse Ig (Pharmingen, San Diego, Calif.). Cells were washed twice after each incubation, and HLA-A2.1 expression was measured by flow cytometry (FACScan; Becton Dickinson, Mountain View, Calif.). HLA-A2.1 expression was quantified by fluorescence index (FI) according to the formula: [FI=(mean fluorescence with peptide−mean fluorescence without peptide)/mean fluorescence without peptide. Background fluorescence without BB7.2 was subtracted for each individual value]. To compare the different peptides, $FI_{0.5}$, the peptide concentration that increases HLA-A2.1 expression by 50% over no peptide control background, was calculated from the titration curve for each peptide.

FIG. 1A is a comparison of the HLA-A2 binding curves among the wild type RT (179-187), VIYQYMDDL (SEQ ID NO:7), RT-1Y (YIYQYMDDL; SEQ ID NO:8), RT-2L9V (VLYQYMDDV; SEQ ID NO:2), and RT-1Y2L9V (YLYQYMDDV; SEQ ID NO:3) in the T2-binding assay.

FIG. 1B compares HLA-A2 binding curves among the RT-2L9V, p17-WT (SLYNTVATL; SEQ ID NO:9), RT-1Y2L9V and FMP (GILGFVFTL; SEQ ID NO:10).

CTL Generation in A2 Kb and HHD-2 Transgenic Mice

Mice more than 8-week-old were immunized subcutaneously at the base of the tail with 100 μl of an emulsion containing 1:1 incomplete Freund's adjuvant (IFA) and PBS solution with antigens and cytokines (50 nmol CTL epitope, 50 nmol HBV core 128-140 helper epitope, 5 μg of IL-12, and 5 μg of granulocyte macrophage colony stimulating factor (GM-CSF)). Mice were boosted 2 wk later, and spleens removed 10-14 days after the boost. Immune spleen cells ($2.5\times10^6$/well) were stimulated in 24-well plates with autologous spleen cells ($5\times10^6$/well) pulsed for 2 h with 10 μM CTL epitope peptide in CTM with 10% T-Stim (Collaborative Biochemical Products, Bedford, Mass.). After more than 4 in vitro stimulations with peptide-pulsed syngeneic spleen cells, CTL lines were maintained by weekly restimulation of $1\times10^6$ CTL/well with $4\times10^6$ peptide pulsed irradiated (3,300 rads) syngeneic spleen cells as feeders, or by weekly stimulation of $1\times10^6$ CTL/well with $3.8\times10^6$ peptide pulsed irradiated C57BL/6 spleen cells and $1\text{-}3\times10^5$ peptide pulsed and irradiated (15,000 rad) Jurkat-A21e transfectant cells.

Cytotoxicity Assay

CTL activity was measured using a 4-h assay with $^{51}Cr$-labeled target cells. Target cells ($10^6$) were pulsed in 100 μl CTM and 150 μCi $^{51}Cr$ for 1.5 h, washed three times, and added at 3,000 cells/well to the 96-well round-bottom plates with different peptide concentrations. Effector cells were added 2 h later, and the supernatants were harvested and counted after an additional 4 h of incubation. The percentage of specific $^{51}Cr$ release was calculated as 100×(experimental release−spontaneous release)/(Maximum release−spontaneous release). Spontaneous release was determined from target cells incubated without effector cells, and maximum release was determined in the presence of 0.1 M HCl. Jurkat-A2$K^b$ lines or C1R.AAD cell lines were used as targets.

IFN-γ and RANTES Assay

IFN-γ and RANTES in the culture supernatant were determined by ELISA kit (R&D, Minneapolis, Mass.) according to the manufacturer's instructions. All samples were analyzed in triplicate.

Protection Assay from Viral Challenge

Female mice were immunized with the same protocol as in the CTL generation protocol described above, boosted i.p. 2 weeks after primary immunization, and challenged i.p. 30 days later with recombinant vaccinia virus ($2\times10^7$ pfu/mouse) expressing HIV reverse transcriptase (vCF21) or β-galactosidase (vSC8). Five days later virus titers in the ovaries of individual mice were determined on BSC-1 indicator cells as previously described (Ahlers, J. D., et al., Int Immunol 13:897).

Example 1

RT Ala-Substituted Peptides Binding to HLA-A2.1 Molecules

This example is designed to determine which residues, other than the anchor residues 2 and 9, are important in RT-WT peptide binding to MHC molecules.

Binding affinity of wild type RT (179-187) (RT-WT) using the T2 binding assay, measuring the cell surface stabilization of HLA-A2.1 molecules after incubation with peptide. Relative affinity for MHC molecules was determined for each peptide in Table 2 by comparing their $FI_{0.5}$ values as calculated from titration curves against HLA-A2 molecules. Using this method, an $FI_{0.5}$ of 41.9 μM was calculated for RT-WT. This binding affinity was much weaker than that of other 9-mer peptides tested in our lab such as hepatitis C virus peptide C7A2 (Sarobe, P., et al., (1998) *J. Clin. Invest.* 102: 1239), Flu matrix peptide 58-66 (FMP) (Gotch, F. M., et al., (1987). *Nature* 326:881.), and HIV-gag peptide SLYNTVATL (SEQ ID NO:9) (McMichael, A. J., and B. D. Walker. (1994), *AIDS* 8 (suppl 1):S155; See also Table 2). In a set of experiments to define key functional residues, peptides with alanine substitutions at each one of the positions were synthesized and tested in binding assays, as described above. The results of these experiments are summarized in Table 2, below.

TABLE 2

Binding of RT (179-187)-wild type and -substituted peptide to HLA-A2.

| Peptide | Sequence | SEQ ID NO: | $FI_{0.5}$ |
|---|---|---|---|
| RT (179-187)-WT | VIYQYMDDL | 7 | 41.9 |
| 1A | **A**IYQYMDDL | 12 | 33.7 |
| 2A | V**A**YQYMDDL | 13 | >100 |
| 3A | VI**A**QYMDDL | 14 | 41.2 |
| 4A | VIY**A**YMDDL | 15 | 40.7 |
| 5A | VIYQ**A**MDDL | 16 | 95.6 |
| 6A | VIYQY**A**DDL | 17 | 17.4 |
| 7A | VIYQYM**A**DL | 18 | >100 |
| 8A | VIYQYMD**A**L | 19 | 35.9 |
| 9A | VIYQYMDD**A** | 20 | 57.9 |
| 2L | V**L**YQYMDDL | 21 | 19.2 |
| 9V | VIYQYMDD**V** | 22 | 19.9 |
| 2L9V (RT-2L9V) | V**L**YQYMDD**V** | 2 | 5.7 |
| gag (p17)(77-85) | SLYNTVATL | 9 | 2.21 |
| Flu-MP (58-66) | GILGFVFTL | 10 | 0.24 |

As indicated in table 2, alanine substitutions at the 2 and 7 positions caused almost complete loss of binding to HLA-A2. Alanine substitution at position 5 also caused a substantial decrease in binding, whereas a moderate decrease in binding was observed when alanine was substituted for leucine at position 9. These data suggest that, in addition to the anchor residues 2 and 9, the amino acid residue at positions 5 and 7 are also important to peptide binding to HLA-A2.

Example 2

Leu and/or Val-Substitution at Anchor Regions in RT-WT

In an attempt to enhance peptide binding to MHC molecules, peptides with substitutions of leucine and/or valine, at the anchor positions 2 and 9 respectively, were synthesized and tested in the binding assay, as described above. The leucine and valine substitutions were chosen because these are the amino acids that predominate at the respective positions in peptides known to bind HLA-A2.1 molecules (Rammensee, H.-G., et al., (1995) *Immunogenetics* 41:178). Peptides substituted with leucine at position 2 or valine at position 9 had around 2-fold higher affinity for HLA-A2 than RT-WT. However, a peptide substituted at both positions, RT-2L9V, had around an 8-fold higher binding affinity for HLA-A2 than RT-WT. This affinity was higher than that of any other alanine-substituted peptides of RT (179-187) tested. (see table 2).

Example 3

Comparison of the Binding Affinity Between Substitutions in Anchor Region and Tyrosine-Substitution in Position 1

Recent studies reported that a Tyrosine substitution in the first position ($P^1Y$) can increase peptide/MHC binding without altering antigenic specificity (Pogue, R. R., et al., (1995) Proc. Natl. Acad. Sci. U.S.A. 92:8166; Tourdot, S., A. et al., (2000) Eur J Immunol 30:3411). Based on these studies, we used the T2 binding assay to compare peptide/MHC binding among 4 derivative peptides:

```
RT-WT,

RT-2L9V,

RT-1Y         (YIYQYMDDL; SEQ ID NO: 8),
and

RT-1Y2L9V     (YLYQYMDDV; SEQ ID NO: 3)
```

As shown in FIG. 1A, RT-2L9V displayed much better binding than the RT-1Y, while both substituted peptides had higher affinity than RT-WT. RT-1Y2L9V displayed the highest affinity of all the peptides. The binding ability of RT-1Y2L9V was almost as good as that of FMP (FIG. 1B). This data suggests that RT-2L9V and RT-1Y2L9V were the best candidates for an epitope enhanced peptide.

Example 4

Recognition of RT-Variant Peptides by CTL Lines Front $A2K^b$- and HHD-2-Transgenic Mice To determine residues involved in CTL recognition, we immunized HLA-A2 transgenic mice, using two different strains.

RT-WT and −2L9V specific CTL lines were separately developed from both A2 Kb and BED-2 transgenic mice, and an RT-1Y2L9V specific CTL line was developed from HHD-2 mice by immunizing the mice with the respective peptides, followed by several rounds (e.g., 5 rounds) of stimulation with each respective peptide. The resulting CTL lines had almost completely non-overlapping Vβ repertoires. (In the case of A2 Kb mice, the RT-WT specific CTL line had Vβ2, 3 and 12 while the RT-2L9V specific CTL line had Vβ3, 4, 5, 8 and 10b. In the case of HHD-2 mice, the RT-WT specific CTL had Vβ8.1 or 8.2 while the RT-2L9V specific CTL had Vβ4, data not shown.)

Figure 2:
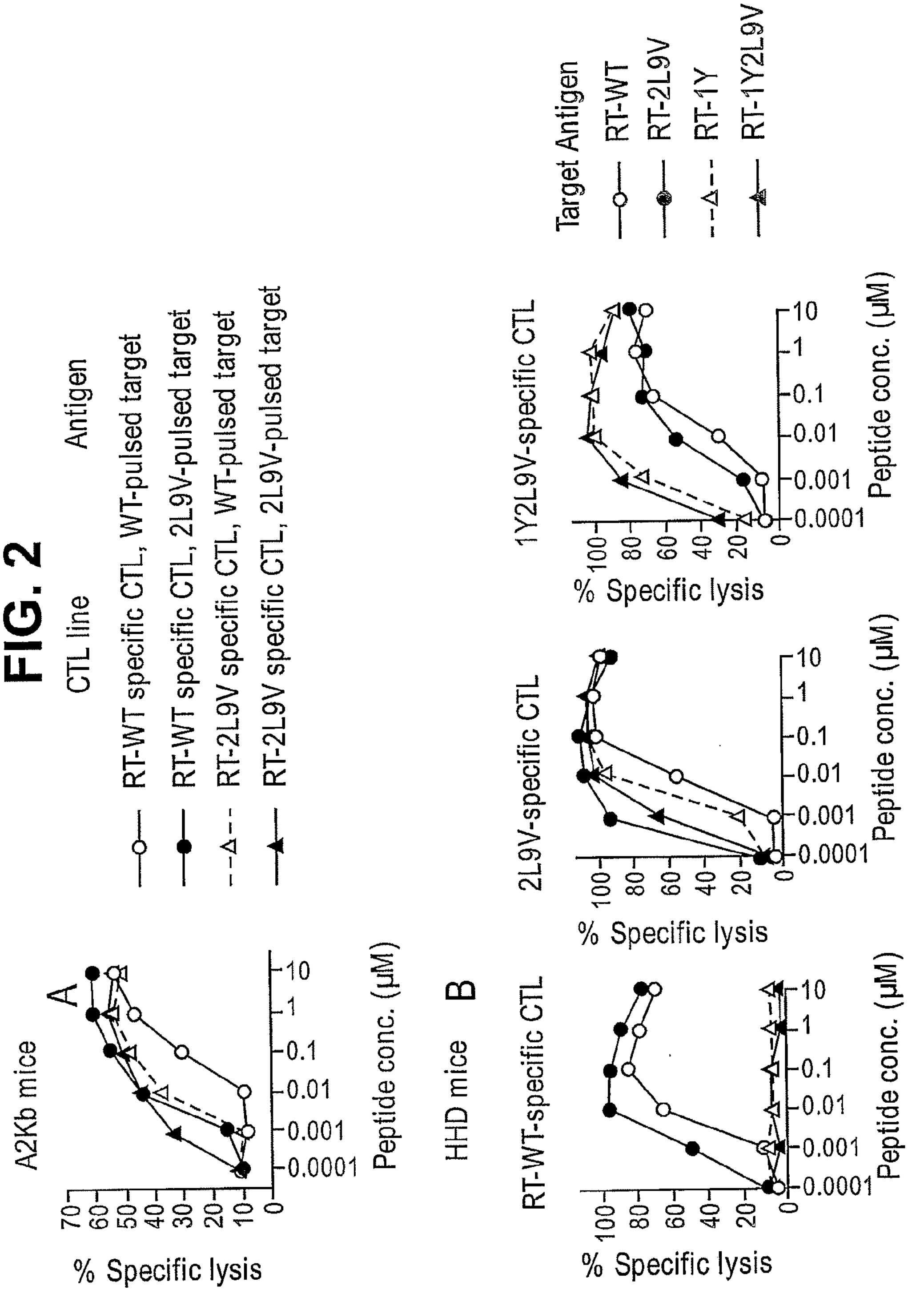
FIG. 2A illustrates the recognition of RT-WT and RT-2L9V peptides by RT-WT and RT-2L9V specific CTL lines from A2 Kb-transgenic mice as a function of peptide concentration, revealing the difference in peptide affinity for HLA-A2 and CTL avidity for the same peptide-MHC complexes. (E/T ratio, 10:1)
FIG. 2B illustrates the recognition of RT-WT, RT-1Y, RT-2L9V and RT-1Y2L9V peptides by RT-WT, RT-2L9V and RT-1Y2L9V specific CTL lines from HHD-2-transgenic mice as a function of peptide concentration, revealing the difference in peptide affinity for HLA-A2 and CTL avidity for the same peptide-MHC complexes. (E/T ratio, 10:1)

Crossreactivity among RT-WT, RT-2L9V and RT-1Y2L9V was checked using the peptide-specific CTL lines (FIG. 2). Jurkat-$A2K^b$ transfectant cells or C1R.AAD cells were used as a target. RT-WT, RT-2L9V and RT-1Y2L9V specific CTL lines killed target cells pulsed with an adequate antigen concentration in an antigen-specific manner. The peptide-specific CTL lines were crossreactive with targets pulsed with the wild type peptide. In the case of A2 Kb-derived CTL lines, RT-2L9V coated targets were killed at lower a concentration than RT-WT-coated targets, consistent with the higher affinity of the RT-2L9V peptide and the crossreactivity of the CTL lines for the two peptides. Unexpectedly, the RT-2L9V-specific CTL line killed RT-WT pulsed targets at more than one log lower peptide concentration than did the line raised against this peptide, indicating that the RT-2L9V peptide also elicited higher avidity CTL.

All 3 peptide-specific HHD-2-derived CTL lines recognized wild type-pulsed targets. RT-2L9V-specific CTL recognized the wild type peptide-pulsed targets to the same extent as the RT-WT specific CTL. However, 1Y2L9V-specific CTL recognition of the wild type peptide-pulsed targets was paradoxically weaker than that by the other two CTL lines (FIG. 2B). Moreover, RT-WT specific CTL did not recognize RT-1Y and RT-1Y2L9V-pulsed targets (FIG. 2B). Furthermore, RT-1Y2L9V-specific CTL recognized targets pulsed with peptides having a tyrosine substitution in position 1 preferentially over peptides not mutated in position 1, even though RT-1Y has lower binding affinity to the HLA-A2 molecule than RT-2L9V in the T2-binding assay.

These data indicate that the difference between V and Y at position 1 can clearly be distinguished by the T cell receptor, and T-cell specificity for V over Y can override the effect of the higher affinity for MHC shown by the peptides substituted at position 1 with tyrosine. This indicates that the amino acid in position 1 of an HLA-A2.1-restricted CD8 epitope could be critical to correct recognition by the T cell receptor, in contrast to the examples disclosed in Tourdot, S., A. et al., (2000) *Eur J Immunol* 30:3411.

In addition, the data indicate that RT-2L9V-specific CTLs derived from HLA-A2 transgenic mice have the same or higher avidity for targets pulsed with RT-WT, when compared to RT-WT specific CTLs.

FIG. 2 is a comparison of antigenic potency by RT-WT, −2L9V and −1Y2L9V CTL lines. FIG. 2A illustrates recognition of RT-WT and RT-2L9V peptides by RT-WT and RT-2L9V specific CTL lines from A2 Kb-transgenic mice as a function of peptide concentration reveals difference in peptide affinity for HLA-A2 and CTL avidity for the same peptide-MHC complexes. (E/T ratio, 10:1). FIG. 2B depicts the recognition of RT-WT, −1Y, −2L9V and −1Y2L9V peptides by RT-WT, −2L9V and −1Y2L9V specific CTL lines from MID-2-transgenic mice as a function of peptide concentration reveals difference in peptide affinity for HLA-A2 and CTL avidity for the same peptide-MHC complexes. (E/T ratio, 10:1)

Example 5

IFN-γ and RANTES Production From the ET-Specific CTL Lines Stimulated by RT-Variant Peptides This example describes tests of the peptide-specific IFN-γ and RANTES production by each peptide-specific CTL line described above, as a function of peptide concentration. These tests allow us to compare inducibility by the RT-WT and substituted peptides of other forms of T cell activity important to the cellular immune response (see FIGS. 3 and 4).

IFN-γ is known to contribute to clearance of recombinant vaccinia virus in mice (Harris, N., R. M. Buller, and G. Karupiah, (1995). *J Virol.* 69:910.). RANTES can inhibit binding of HIV to its coreceptor, CCR5 (Cocchi, F., A. L. et al., (1995) *Science* 270:1811). In A2 Kb mice, the RT-2L9V peptide induced more IFN-γ production by the RT-WT specific CTL line than the RT-WT peptide itself, as the peptide concentration was reduced. The CTL raised against RT-2L9V also appeared to have higher avidity for the RT-WT peptide than the CTL raised against the wild type peptide itself, in that the titration curve for RT-WT was shifted and the difference in the IFN-γ production by these two CTL lines from A2 Kb mice induced by the same RT-WT peptide was more than 100-fold at 0.1 μM of peptide (FIG. 3A). The RT-2L9V peptide also could induce more IFN-γ production by the RT-2L9V specific CTL line than the RT-WT peptide.

In HHD mice, IFN-γ production from the RT-1Y2L9V specific CTL line was parallel to the binding ability of the peptide to HLA-A2. However, the antigen-specific IFN-γ production by RT-2L9V specific CTL was better when stimulated with RT-2L9V than with RT-1Y2L9V. The RT-2L9V specific CTL line also produced about 10 times more IFN-γ compared to the RT-1Y2L9V specific CTL when stimulated with the wild type peptide (FIG. 3B).

RANTES (Regulated upon Activation, Normal T expressed, and presumably Secreted) is a member of the CC chemokine family of inflammatory and immunoregulatory chemokines. RANTES is also produced by stimulated CTL and has been shown to inhibit HIV infection of human mononuclear cells (Cocchi, F., A. L. et al., (1995) *Science* 270: 1811). Production of this chemokine by CTL therefore could be one of the parameters for effector activity in HIV infection.

As shown in FIGS. 4A and 4B, RANTES was produced by all CTL lines in an antigen-specific manner. In A2 Kb mice, RANTES production by RT-WT specific CTL decreased to background levels at 0.1 μM peptide. In contrast, RANTES production by RT-2L9V specific CTL remained strong, regardless of which peptide was stimulatory (FIG. 4A). These data suggest that the RT-2L9V-substituted peptide has higher avidity for wild-type specific CTL than the wild type peptide, whereas the crossreactivity of RT-1Y2L9V-specific CTL for wild-type peptide is significantly weaker (FIG. 4B).

Figure 3:
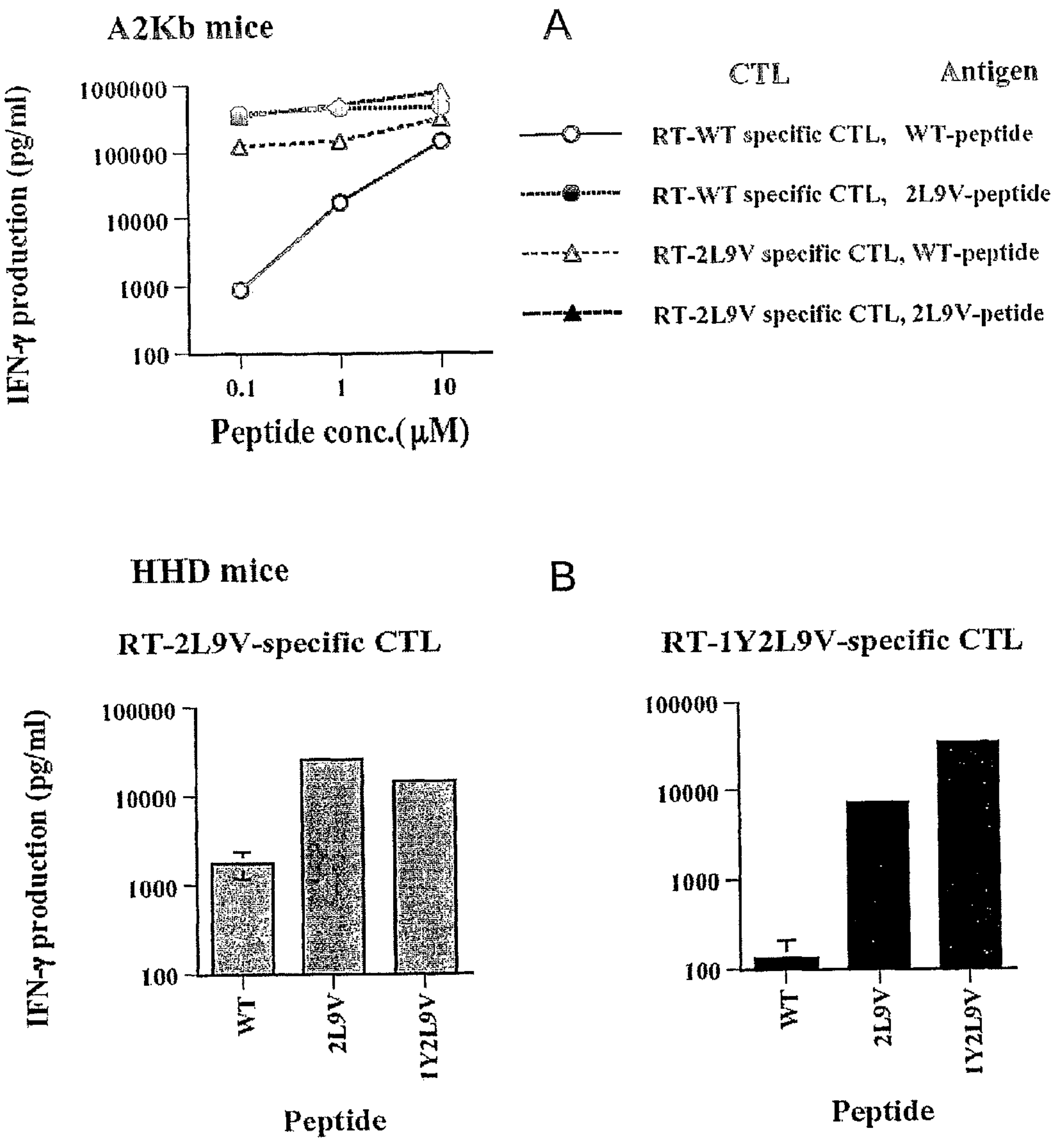
FIG. 3A illustrates IFN-γ production by RT-WT and −2L9V specific CTL line derived from A2 Kb-transgenic mice.
FIG. 3B illustrates IFN-γ production by RT-2L9V and −1Y2L9V specific CTL line derived from HHD-2-transgenic mice.
Figure 4:
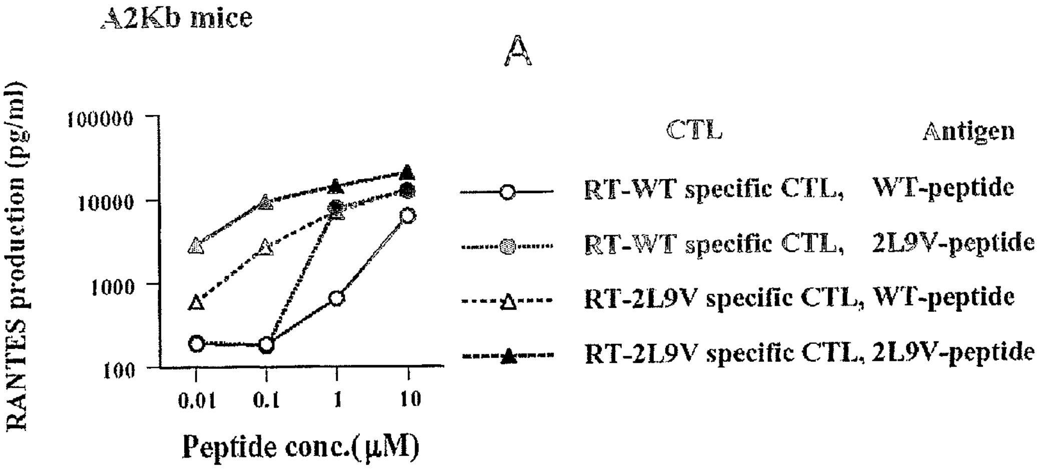
FIG. 4A illustrates RANTES production by RT-WT and RT-2L9V specific CTL line derived from A2 Kb-transgenic mice.
FIG. 4B illustrates RANTES production by RT-2L9V and −1Y2L9V specific CTL line derived from HHD-2-transgenic mice.
Figure 4:
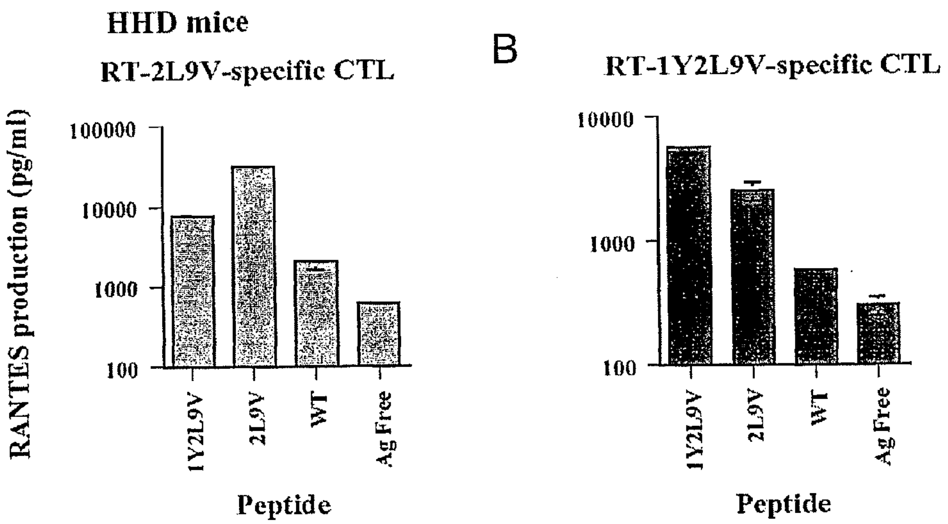

FIG. 3 is a comparison of IFN-γ and RANTES production induced by RT-WT, −2L9V and −1Y2L9V peptides. After being pulsed with different peptide concentrations for 2 h, Jurkat-A2K$^b$ cells were irradiated at 15,000 rad and plated at a hundred thousand cells/well in 96-well round-bottom plates. Five hundred thousand CTLs were added into each well, and the supernatants were harvested at 48 h. IFN-γ in the culture supernatant was determined by ELISA kit according to the manufacturer's instructions. All samples were used at 2-640-fold dilution and analyzed in triplicate. FIG. 3A graphically illustrates IFN-γ production by RT-WT and −2L9V specific CTL line derived from A2 Kb-transgenic mice. FIG. 3B shows the IFN-γ production by RT-2L9V and −1Y2L9V specific CTL line derived from HHD-2-transgenic mice.

FIG. 4A compares RANTES production by RT-WT and −2L9V specific CTL line derived from A2 Kb-transgenic mice, while FIG. 4B compares RANTES production by RT-2L9V and −1Y2L9V specific CTL line derived from HHD-2-transgenic mice.

Example 6

Figure 5:
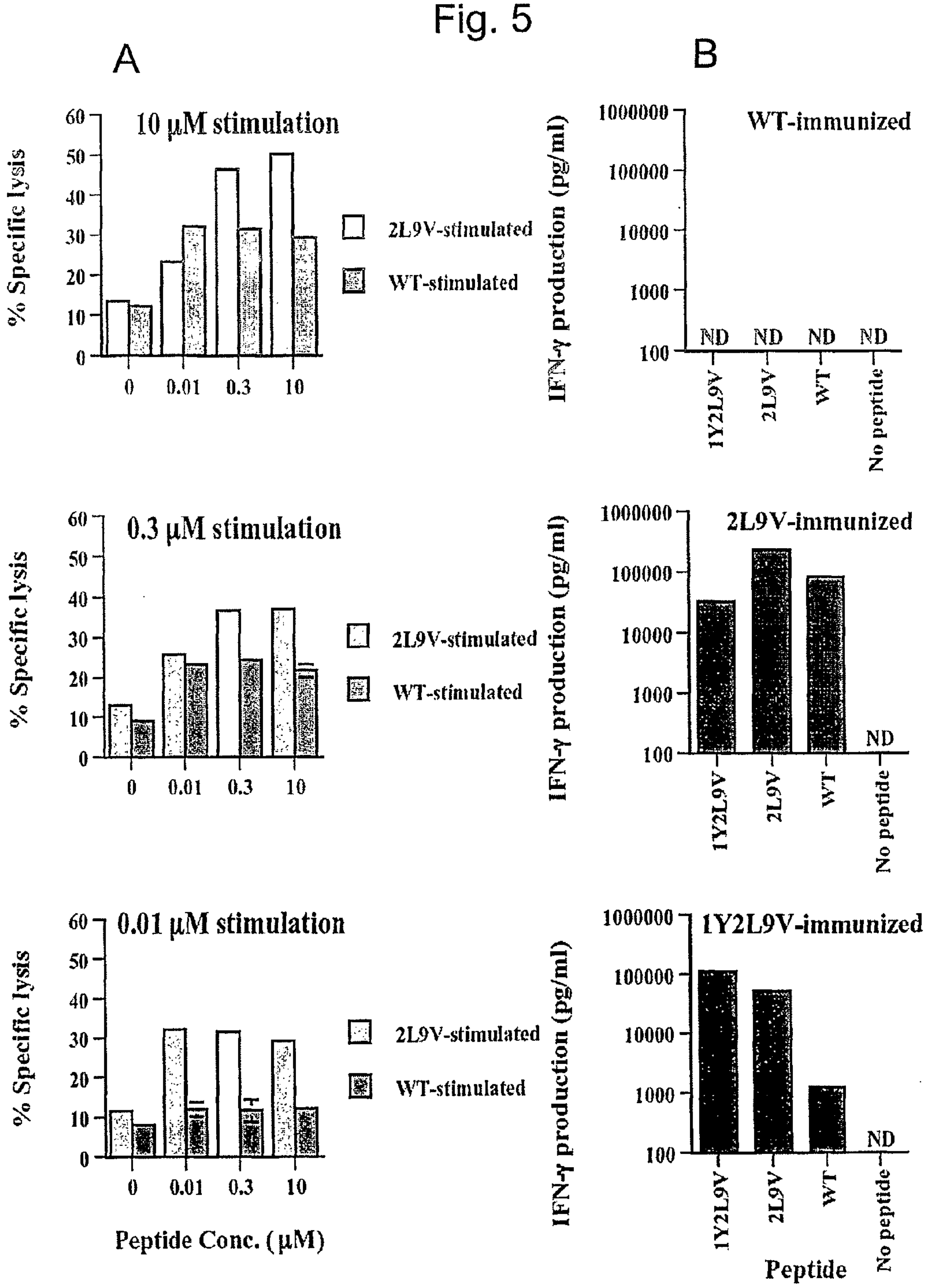
FIG. 5A illustrates induction of CTL immune response and comparison of CTL avidity against RT-WT in A2 Kb-transgenic mice using different RT peptide variants.
FIG. 5B illustrates induction of antigen specific IFN-γ production by peptides-specific culture lines.

In Vivo Immunogenicity of RT-2L9V and −1Y2L9V Peptide in HLA-A2 Transgenic Mice This example compares the in vivo immunogenicity of the RT-RW, RT-2L9V, and the RT-1Y2L9V peptides in the A2K$^b$ and HHD-2 transgenic mouse models. To test the ability of RT-WT and RT-2L9V peptides to induce a CTL immune response against RT-WT in A2 Kb mice, different groups of animals were immunized with RT-WT or RT-2L9V-substituted peptides in conjunction with a helper epitope and cytokines as described in the General Methods, above. The ability of these peptides to induce an immune response was tested in CTL assays after giving the animals booster injections with an adequate concentration of the respective peptides (FIG. 5A). Both RT-WT and RT-2L9V peptides induced immune responses after stimulation with higher peptide concentrations (10 μM and 0.3 μM respectively), but RT-2L9V induced a more vigorous CTL immune response than RT-WT. Dosing with 0.01 μM RT-WT failed to raise a CTL response above background levels. 0.01 μM RT-2L9V however was sufficient to induce a CTL response against a RT-WT-pulsed target. These results indicate that RT-2L9V induces a stronger CTL response against a RT-WT-pulsed target than RT-WT. Moreover, surprisingly, the CTL response induced by RT-2L9V recognizes RT-WT-pulsed targets better than the CTL response induced by RT-WT.

In addition, further tests, using antigen-specific IFN-γ production as a marker, demonstrated that tyrosine substitution at position 1 adversely affects CTL induction against RT-WT-pulsed targets, despite eliciting a strong CTL response against targets pulsed with the peptide having the position 1 tyrosine substitution.

HHD-2 mice were immunized twice with 50 nmol peptide and cytokines in IFA as previously described and immune spleen cells were stimulated with syngeneic spleen cells that had been pulsed with 10 μM peptide and irradiated. After one week, short-term cultures were stimulated, each with one of the three peptides. After 48 hr, IFN-γ production for each culture was determined by measuring the culture supernatant IFN-γ concentration.

No antigen-specific IFN-γ production could be detected in RT-WT immunized bulk culture using this system. Surprisingly, both RT-2L9V and RT-1Y2L9V-immunized bulk culture induced much higher IFN-γ production (FIG. 5B). Each culture responded best to the peptide used stimulate it. Moreover, IFN-γ produced by RT-2L9V immunized bulk culture against the RT-WT was about 70-fold higher than that produced by the RT-1Y2L9V culture, despite RT-1Y2L9V displaying much stronger binding to HLA-A2 than RT-2L9V. These data suggest that tyrosine substitution at position 1 adversely affects CTL induction against RT-WT-pulsed targets, despite eliciting a strong CTL response against targets pulsed with the peptide having the position 1 tyrosine substitution.

FIG. 5A shows the induction of CTL immune response and comparison of CTL avidity against RT-WT in A2 Kb-transgenic mice using different RT peptide variants. A2 Kb-transgenic mice were immunized with 50 nmol CTL epitope RT-WT or −2L9V plus 50 nmol HBVc 128-140 helper epitope and 5 μg IL-12 and GM-CSF in IFA. 2 wk later, they were boosted under the same conditions, and 10-14 days after the boost, spleen cells were removed and stimulated separately in vitro with 10, 0.3 and 0.01 μM CTL peptide-pulsed spleen cells. A week after the 2$^{nd}$ stimulation in culture, a cytotoxic assay was performed with each concentration of RT-WT peptide. FIG. 5B illustrates induction of antigen specific IFN-γ production by the peptide-specific CTL. HHD-2-transgenic mice were immunized with 50 nmol CTL epitope RT-WT, −2L9V or −1T2L9V plus 50 nmol HBVc 128-140 helper epitope and 5 μg IL-12 and GM-CSF in IFA. 2 wk later, they were boosted under the same conditions, and 10-14 days after the boost, spleen cells were removed and stimulated separately in vitro with irradiated spleen cells pulsed with the optimum concentration of each peptide. 9 days after the stimulation, the cultured cells were restimulated with each peptide. Each supernatant was assayed for IFN-γ by ELISA 48 hr later.

Example 7

Protection Ability of Epitope Enhanced Peptides In Vivo

To determine the ability of RT-2L9V and RT-1Y2L9V to protect against viral infection in vivo, different populations of HHD-2 mice (described above) were immunized with RT-2L9V and RT-1Y2L9V, respectively. Both populations were then challenged with vaccinia virus (vCF21) expressing RT protein as a surrogate to challenge HIV-1 virus. This surrogate approach was necessary as the HLA-A2.1 transgenic mice cannot be infected with HIV-1 itself. HHD-2 mice were specifically selected for this study because the only class I molecule they express is HLA-A2.1 (Pascolo, S., N. et al., (1997) *J. Exp. Med.* 185:2043), so protection cannot be mediated by CTL restricted to =nine MHC molecules. As a control, populations of HHD-2 mice, immunized with RT-2L9V and RT-1Y2L9V respectively, were challenged with a second vaccinia strain (vSC8) that does not express RT. Neither population of mice displayed protection against vaccinia infection.

Figure 6:
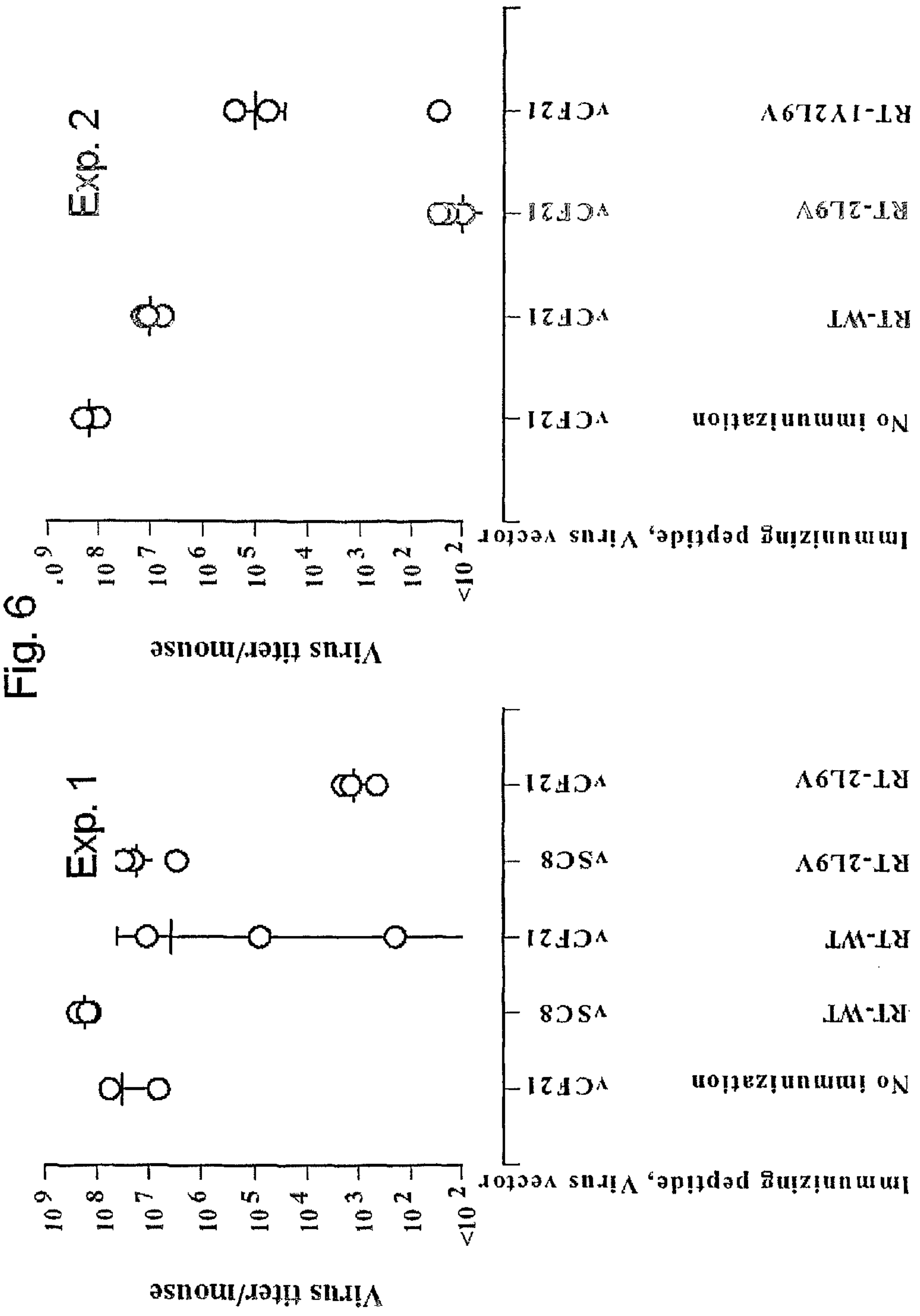
FIG. 6 graphically depicts the protection induced by immunization with RT-peptides.

FIG. 6 shows the protection induced by immunization with RT-peptides. On day 30 after the last immunization, female MD-2 mice, expressing only the human HLA-A2.1 class I molecule and no murine class I molecules, were challenged intraperitoneally with $2\times10^7$ pfu of vaccinia virus expressing a reverse transcriptase protein of HIV (vCF21) or a β-galactosidase protein (vSC8). Five days later, virus titers in the ovaries were determined FIG. 6 illustrates that, in both protection assays, RT-2L9V-immunized mice were protected against vCF21 infection, resulting in a 4-5 log reduction in virus titer (Exp. 1) or complete protection (6 log reduction) (Exp. 2) compared to unimmunized control animals ($p<0.01$). In contrast, RT-1Y2L9V-immunized mice were only partially protected.

These data confirm that RT-2L9V is more a better vaccine candidate than the wild type peptide, RT-WT. RT-2L9V is also shown to be a better vaccine candidate than RT-1Y2L9V, even though RT-1Y2L9V has much higher binding affinity to HLA-A2 than RT-2L9V.

To ensure a full description of the invention, all publications and patent applications cited in this specification are herein incorporated by reference as if each individual publication or patent application were specifically and individually indicated to be incorporated by reference.

What is claimed is:

1. A composition comprising a vector including a nucleic acid comprising a nucleotide sequence encoding an immunogenic polypeptide comprising the HIV-1 RT CTL epitope $X_1$LYQYMDDV (SEQ ID NO: 1), wherein $X_1$ is any hydrophobic amino acid, and wherein the vector results in expression of the immunogenic polypeptide and the induction of an anti-HIV-1 immune response against the CTL epitope of SEQ ID NO: 1, when the composition is introduced into a host.

2. The composition of claim 1, wherein the vector is a virus.

* * * * *